United States Patent
DeFreitas et al.

(10) Patent No.: US 11,096,644 B2
(45) Date of Patent: Aug. 24, 2021

(54) X-RAY MAMMOGRAPHY WITH TOMOSYNTHESIS

(71) Applicant: Hologic, Inc., Marlborough, MA (US)

(72) Inventors: Kenneth DeFreitas, Patterson, NY (US); Baorui Ren, Andover, MA (US); Ian Shaw, Yorktown Heights, NY (US); Christopher Ruth, Danvers, MA (US); Andrew P. Smith, Lexington, MA (US); Jay A. Stein, Boston, MA (US)

(73) Assignee: Hologic, Inc., Marlborough, MA (US)

( * ) Notice: Subject to any disclaimer, the term of this patent is extended or adjusted under 35 U.S.C. 154(b) by 573 days.

(21) Appl. No.: 16/004,151

(22) Filed: Jun. 8, 2018

(65) Prior Publication Data

US 2018/0344276 A1    Dec. 6, 2018

Related U.S. Application Data

(60) Continuation of application No. 13/896,828, filed on May 17, 2013, now Pat. No. 10,638,994, which is a
(Continued)

(51) Int. Cl.
*A61B 6/00* (2006.01)
*A61B 6/02* (2006.01)
*A61B 6/04* (2006.01)

(52) U.S. Cl.
CPC .............. *A61B 6/502* (2013.01); *A61B 6/025* (2013.01); *A61B 6/0414* (2013.01);
(Continued)

(58) Field of Classification Search
CPC ......... A61B 6/025; A61B 6/0414; A61B 6/12; A61B 6/42; A61B 6/4447; A61B 6/461;
(Continued)

(56) References Cited

U.S. PATENT DOCUMENTS 3,365,575 A    1/1968  Strax
3,502,878 A    3/1970  Stewart
(Continued)

FOREIGN PATENT DOCUMENTS

CN    102222594    10/2011
DE     4104166     8/1992
(Continued)

OTHER PUBLICATIONS

Niklason, Loren T., Bradley T. Christian, Laura E. Niklason, Daniel B. Kopans, Priscilla J. Slanetz, Donald E. Castleberry, Beale H. Opsahl-Ong, Cynthia E. Landberg, and Brian Giambattista. "Digital breast tomosynthesis: potentially a new method for breast cancer screening." In Digital Mammography (Year: 1998).*

(Continued)

*Primary Examiner* — Carolyn A Pehlke

(57) ABSTRACT

A method and system for producing tomosynthetic images of a patient's breast. An x-ray source that delivers x-rays through a breast immobilized and compressed between a compression paddle and a breast platform and form an image at a digital x-ray receptor panel. Multiple x-ray images are taken as the x-ray source and the receptor move relative to the immobilized breast. In one preferred embodiment, the x-ray source travels from −15° to +15°. The source can travel in an arc around the breast while the receptor travels linearly while remaining parallel and at the same distance from the breast platform. The sets of x-ray image data taken at different angles are combined to form tomosynthetic images that can be viewed in different formats, alone or as an adjunct to conventional mammograms.

18 Claims, 5 Drawing Sheets

Related U.S. Application Data continuation of application No. 12/879,807, filed on Sep. 10, 2010, now Pat. No. 8,452,379, which is a division of application No. 10/723,486, filed on Nov. 26, 2003, now Pat. No. 7,831,296.

(52) U.S. Cl.
CPC ........... *A61B 6/4291* (2013.01); *A61B 6/4441* (2013.01); *A61B 6/464* (2013.01); *A61B 6/481* (2013.01); *A61B 6/482* (2013.01)

(58) Field of Classification Search
CPC ........... A61B 6/464; A61B 6/502; A61B 6/48; A61B 6/481; A61B 6/482; A61B 6/52; A61B 6/5205; A61B 6/5211
See application file for complete search history.

(56) References Cited

U.S. PATENT DOCUMENTS

| | | |
|---|---|---|
| 3,863,073 A | 1/1975 | Wagner |
| 3,971,950 A | 7/1976 | Evans et al. |
| 4,160,906 A | 7/1979 | Daniels et al. |
| 4,310,766 A | 1/1982 | Finkenzeller et al. |
| 4,380,086 A | 4/1983 | Vagi |
| 4,496,557 A | 1/1985 | Malen et al. |
| 4,513,433 A | 4/1985 | Weiss et al. |
| 4,542,521 A | 9/1985 | Hahn et al. |
| 4,559,641 A | 12/1985 | Caugant et al. |
| 4,662,379 A | 5/1987 | Macovski |
| 4,706,269 A | 11/1987 | Reina et al. |
| 4,721,856 A | 1/1988 | Saotome et al. |
| 4,744,099 A | 5/1988 | Huettenrauch et al. |
| 4,752,948 A | 6/1988 | MacMahon |
| 4,760,589 A | 7/1988 | Siczek |
| 4,763,343 A | 8/1988 | Yanaki |
| 4,773,086 A | 9/1988 | Fujita et al. |
| 4,773,087 A | 9/1988 | Plewes |
| 4,819,258 A | 4/1989 | Kleinman et al. |
| 4,821,727 A | 4/1989 | Levene et al. |
| 4,901,335 A | 2/1990 | Ferlic |
| 4,969,174 A | 11/1990 | Scheid et al. |
| 4,989,227 A | 1/1991 | Tirelli et al. |
| 4,998,270 A | 3/1991 | Scheid et al. |
| 5,018,176 A | 5/1991 | Romeas et al. |
| RE33,634 E | 7/1991 | Yanaki |
| 5,029,193 A | 7/1991 | Saffer |
| 5,051,904 A | 9/1991 | Griffith |
| 5,078,142 A | 1/1992 | Siczek et al. |
| 5,142,557 A | 8/1992 | Toker |
| 5,163,075 A | 11/1992 | Lubinsky et al. |
| 5,164,976 A | 11/1992 | Scheid et al. |
| 5,199,056 A | 3/1993 | Darrah |
| 5,212,637 A | 5/1993 | Saxena |
| 5,240,011 A | 8/1993 | Assa |
| 5,256,370 A | 10/1993 | Slattery et al. |
| 5,274,690 A | 12/1993 | Burke |
| 5,289,520 A | 2/1994 | Pellegrino et al. |
| 5,291,539 A | 3/1994 | Thumann et al. |
| 5,313,510 A | 5/1994 | Ebersberger |
| 5,359,637 A | 10/1994 | Webber |
| 5,365,562 A | 11/1994 | Toker |
| 5,415,169 A | 5/1995 | Siczek et al. |
| 5,426,685 A | 6/1995 | Pellegrino et al. |
| 5,451,789 A | 9/1995 | Wong |
| 5,452,367 A | 9/1995 | Bick et al. |
| 5,479,927 A | 1/1996 | Shmulewitz |
| 5,483,072 A | 1/1996 | Coe |
| 5,506,877 A | 4/1996 | Niklason et al. |
| 5,526,394 A | 6/1996 | Siczek et al. |
| 5,528,658 A | 6/1996 | Hell |
| 5,539,797 A | 7/1996 | Heidsieck et al. |
| 5,553,111 A | 9/1996 | Moore et al. |
| 5,592,562 A | 1/1997 | Rooks |
| 5,594,769 A | 1/1997 | Pellegrino et al. |
| 5,596,200 A | 1/1997 | Sharma et al. |
| 5,598,454 A | 1/1997 | Franetzki et al. |
| 5,606,589 A | 2/1997 | Pellegrino et al. |
| 5,609,152 A | 3/1997 | Pellegrino et al. |
| 5,627,869 A | 5/1997 | Andrew et al. |
| 5,657,362 A | 8/1997 | Giger et al. |
| 5,668,844 A | 9/1997 | Webber |
| 5,668,889 A | 9/1997 | Hara |
| 5,706,327 A | 1/1998 | Adamkowski et al. |
| 5,719,952 A | 2/1998 | Rooks |
| 5,735,264 A | 4/1998 | Siczek et al. |
| 5,769,086 A | 6/1998 | Ritchart et al. |
| 5,803,912 A | 9/1998 | Siczek et al. |
| 5,818,898 A | 10/1998 | Tsukamoto et al. |
| 5,828,722 A | 10/1998 | Ploetz et al. |
| 5,841,829 A | 11/1998 | Dolazza |
| 5,844,242 A | 12/1998 | Jalink, Jr. |
| 5,844,965 A | 12/1998 | Galkin |
| 5,864,146 A | 1/1999 | Karellas |
| 5,872,828 A * | 2/1999 | Niklason ............... A61B 6/025 378/23 |
| 5,878,104 A | 3/1999 | Ploetz |
| 5,896,437 A | 4/1999 | Ploetz |
| 5,930,330 A | 7/1999 | Wolfe |
| 5,941,832 A | 8/1999 | Tumey et al. |
| 5,970,118 A | 10/1999 | Sokolov |
| 5,983,123 A | 11/1999 | Shmulewitz |
| 5,986,662 A | 11/1999 | Argiro et al. |
| 5,999,836 A | 12/1999 | Nelson et al. |
| 6,005,907 A | 12/1999 | Ploetz |
| 6,022,325 A | 2/2000 | Siczek et al. |
| 6,075,879 A | 6/2000 | Roehrig et al. |
| 6,081,577 A | 6/2000 | Webber |
| 6,091,841 A | 7/2000 | Rogers et al. |
| 6,137,527 A | 10/2000 | Abdel-Malek et al. |
| 6,141,398 A | 10/2000 | He et al. |
| 6,149,301 A | 11/2000 | Kautzer et al. |
| 6,167,115 A * | 12/2000 | Inoue ..................... G21K 1/025 378/154 |
| 6,175,117 B1 | 1/2001 | Komardin et al. |
| 6,196,715 B1 | 3/2001 | Nambu et al. |
| 6,207,958 B1 | 3/2001 | Giakos |
| 6,216,540 B1 | 4/2001 | Nelson et al. |
| 6,219,059 B1 | 4/2001 | Argiro |
| 6,233,473 B1 | 5/2001 | Shepherd et al. |
| 6,243,441 B1 | 6/2001 | Zur |
| 6,244,507 B1 | 6/2001 | Garland |
| 6,256,369 B1 | 7/2001 | Lai |
| 6,256,370 B1 | 7/2001 | Yavuz |
| 6,269,176 B1 | 7/2001 | Barski |
| 6,272,207 B1 | 8/2001 | Tang |
| 6,282,264 B1 | 8/2001 | Smith |
| 6,289,235 B1 | 9/2001 | Webber et al. |
| 6,292,530 B1 | 9/2001 | Yavus et al. |
| 6,292,531 B1 | 9/2001 | Hsieh et al. |
| 6,327,336 B1 | 12/2001 | Gingold et al. |
| 6,341,156 B1 | 1/2002 | Baetz et al. |
| 6,345,194 B1 | 2/2002 | Nelson et al. |
| 6,375,352 B1 | 4/2002 | Hewes et al. |
| 6,399,951 B1 | 6/2002 | Paulus |
| 6,411,836 B1 | 6/2002 | Patel et al. |
| 6,415,015 B2 | 7/2002 | Nicolas et al. |
| 6,418,189 B1 | 7/2002 | Schafer |
| 6,442,288 B1 | 8/2002 | Haerer et al. |
| 6,459,925 B1 | 10/2002 | Nields et al. |
| 6,463,181 B2 | 10/2002 | Duarte |
| 6,480,565 B1 | 11/2002 | Ning |
| 6,490,476 B1 | 12/2002 | Townsend et al. |
| 6,496,557 B2 | 12/2002 | Wilson |
| 6,501,819 B2 | 12/2002 | Unger et al. |
| 6,542,575 B1 | 4/2003 | Schubert |
| 6,553,096 B1 | 4/2003 | Zhou et al. |
| 6,556,655 B1 | 4/2003 | Chichereau et al. |
| 6,574,304 B1 | 6/2003 | Hsieh et al. |
| 6,574,629 B1 | 6/2003 | Cooke, Jr. et al. |
| 6,597,762 B1 | 7/2003 | Ferrant et al. |
| 6,611,575 B1 | 8/2003 | Alyassin et al. |
| 6,620,111 B2 | 9/2003 | Stephens et al. |
| 6,626,849 B2 | 9/2003 | Huitema et al. |

(56) References Cited

U.S. PATENT DOCUMENTS

| | | |
|---|---|---|
| 6,632,020 B2 | 10/2003 | Kaufhold |
| 6,633,626 B2 | 10/2003 | Trotter |
| 6,633,674 B1 | 10/2003 | Barnes et al. |
| 6,638,235 B2 | 10/2003 | Miller et al. |
| 6,647,092 B2 | 11/2003 | Eberhard et al. |
| 6,674,835 B2 | 1/2004 | Kaufhold |
| 6,702,459 B2 | 3/2004 | Barnes et al. |
| 6,744,848 B2 | 6/2004 | Stanton et al. |
| 6,748,044 B2 | 6/2004 | Sabol et al. |
| 6,748,046 B2 | 6/2004 | Thayer |
| 6,748,047 B2 | 6/2004 | Gonzalez |
| 6,751,285 B2 | 6/2004 | Eberhard et al. |
| 6,758,824 B1 | 7/2004 | Miller et al. |
| 6,813,334 B2 | 11/2004 | Koppe et al. |
| 6,846,289 B2 | 1/2005 | Besson |
| 6,882,700 B2 | 4/2005 | Wang et al. |
| 6,885,724 B2 | 4/2005 | Li et al. |
| 6,895,076 B2 | 5/2005 | Halsmer |
| 6,901,132 B2 | 5/2005 | Eberhard |
| 6,909,790 B2 | 6/2005 | Tumey et al. |
| 6,909,792 B1 | 6/2005 | Carrott et al. |
| 6,912,319 B1 | 6/2005 | Barnes et al. |
| 6,931,093 B2 | 8/2005 | Op De Beek et al. |
| 6,940,943 B2 | 9/2005 | Claus et al. |
| 6,950,492 B2 | 9/2005 | Besson |
| 6,950,493 B2 | 9/2005 | Besson |
| 6,957,099 B1 | 10/2005 | Arnone et al. |
| 6,960,020 B2 | 11/2005 | Lai |
| 6,970,531 B2 | 11/2005 | Eberhard et al. |
| 6,970,586 B2 | 11/2005 | Baertsch |
| 6,978,040 B2 | 12/2005 | Berestov |
| 6,987,831 B2 | 1/2006 | Ning |
| 6,999,554 B2 | 2/2006 | Mertelmeier |
| 7,001,071 B2 | 2/2006 | Deuringer |
| 7,016,461 B2 | 3/2006 | Rotondo |
| 7,092,482 B2 | 8/2006 | Besson |
| 7,110,490 B2 | 9/2006 | Eberhard et al. |
| 7,110,502 B2 | 9/2006 | Tsuji |
| 7,116,749 B2 | 10/2006 | Besson |
| 7,123,684 B2 | 10/2006 | Jing et al. |
| 7,127,091 B2 | 10/2006 | Op De Beek et al. |
| 7,142,633 B2 | 11/2006 | Eberhard et al. |
| 7,190,758 B2 | 3/2007 | Hagiwara |
| 7,206,462 B1 | 4/2007 | Betke |
| 7,218,766 B2 | 5/2007 | Eberhard |
| 7,244,063 B2 | 7/2007 | Eberhard |
| 7,245,694 B2 | 7/2007 | Jing et al. |
| 7,263,214 B2 | 8/2007 | Uppaluri |
| 7,286,645 B2 | 10/2007 | Freudenberger |
| 7,302,031 B2 | 11/2007 | Hjarn et al. |
| 7,315,607 B2 | 1/2008 | Ramsauer |
| 7,319,734 B2 | 1/2008 | Besson |
| 7,319,735 B2 | 1/2008 | Defreitas et al. |
| 7,319,736 B2 | 1/2008 | Rotondo |
| 7,323,692 B2 | 1/2008 | Rowlands et al. |
| 7,331,264 B2 | 2/2008 | Ozawa |
| 7,356,113 B2 | 4/2008 | Wu |
| 7,430,272 B2 | 9/2008 | Jing et al. |
| 7,433,507 B2 | 10/2008 | Jabri |
| 7,443,949 B2 | 10/2008 | Defreitas et al. |
| 7,577,282 B2 | 8/2009 | Gkanatsios et al. |
| 7,583,786 B2 | 9/2009 | Jing et al. |
| 7,609,806 B2 | 10/2009 | Defreitas et al. |
| 7,609,808 B2 | 10/2009 | Tornai |
| 7,616,731 B2 | 11/2009 | Pack |
| 7,616,801 B2 | 11/2009 | Gkanatsios et al. |
| 7,630,531 B2 | 12/2009 | Chui |
| 7,630,533 B2 | 12/2009 | Ruth et al. |
| 7,688,940 B2 | 3/2010 | Defreitas et al. |
| 7,697,660 B2 | 4/2010 | Ning |
| 7,702,142 B2 | 4/2010 | Ren et al. |
| 7,760,853 B2 | 7/2010 | Jing et al. |
| 7,760,924 B2 | 7/2010 | Ruth et al. |
| 7,792,245 B2 | 9/2010 | Hitzke et al. |
| 7,831,296 B2 | 11/2010 | Defreitas et al. |
| 7,839,979 B2 | 11/2010 | Hauttmann |
| 7,869,563 B2 | 1/2011 | Defreitas et al. |
| 7,869,862 B2 | 1/2011 | Seppi |
| 7,881,428 B2 | 2/2011 | Jing et al. |
| 7,885,384 B2 | 2/2011 | Mannar |
| 7,894,646 B2 | 2/2011 | Shirahata et al. |
| 7,916,915 B2 | 3/2011 | Gkanatsios et al. |
| 7,949,091 B2 | 5/2011 | Jing et al. |
| 7,986,765 B2 | 7/2011 | Defreitas et al. |
| 7,991,106 B2 | 8/2011 | Ren et al. |
| 8,031,834 B2 | 10/2011 | Ludwig |
| 8,131,049 B2 | 3/2012 | Ruth et al. |
| 8,155,421 B2 | 4/2012 | Ren et al. |
| 8,170,320 B2 | 5/2012 | Smith et al. |
| 8,175,219 B2 | 5/2012 | Defreitas et al. |
| 8,285,020 B2 | 10/2012 | Gkanatsios et al. |
| 8,416,915 B2 | 4/2013 | Jing et al. |
| 8,452,379 B2 | 5/2013 | DeFreitas et al. |
| 8,457,282 B2 | 6/2013 | Baorui et al. |
| 8,515,005 B2 | 8/2013 | Ren et al. |
| 8,559,595 B2 | 10/2013 | Defreitas et al. |
| 8,565,372 B2 | 10/2013 | Stein et al. |
| 8,565,374 B2 | 10/2013 | DeFreitas et al. |
| 8,565,860 B2 | 10/2013 | Kimchy |
| 8,571,289 B2 | 10/2013 | Ruth et al. |
| 8,712,127 B2 | 4/2014 | Ren et al. |
| 8,767,911 B2 | 7/2014 | Ren et al. |
| 8,787,522 B2 | 7/2014 | Smith et al. |
| 8,831,171 B2 | 9/2014 | Jing et al. |
| 8,853,635 B2 | 10/2014 | O'Connor |
| 8,873,716 B2 | 10/2014 | Ren et al. |
| 9,042,612 B2 | 5/2015 | Gkanatsios et al. |
| 9,226,721 B2 | 1/2016 | Ren et al. |
| 9,502,148 B2 | 11/2016 | Ren |
| 9,895,115 B2 | 2/2018 | Ren |
| 10,719,223 B2 | 7/2020 | Gkanatsios |
| 2001/0038681 A1 | 11/2001 | Stanton et al. |
| 2002/0012450 A1 | 1/2002 | Tsujii |
| 2002/0048343 A1 | 4/2002 | Launay et al. |
| 2002/0050986 A1 | 5/2002 | Inouc et al. |
| 2002/0070970 A1 | 6/2002 | Wood et al. |
| 2002/0075997 A1 | 6/2002 | Unger et al. |
| 2002/0090055 A1 | 7/2002 | Zur et al. |
| 2002/0094062 A1 | 7/2002 | Dolazza |
| 2002/0122533 A1 | 9/2002 | Marie et al. |
| 2002/0126798 A1 | 9/2002 | Harris |
| 2003/0007598 A1 | 1/2003 | Wang et al. |
| 2003/0010923 A1 | 1/2003 | Zur |
| 2003/0018272 A1 | 1/2003 | Treado et al. |
| 2003/0026386 A1 | 2/2003 | Tang et al. |
| 2003/0058989 A1 | 3/2003 | Rotondo |
| 2003/0072409 A1 | 4/2003 | Kaufhold et al. |
| 2003/0072417 A1 | 4/2003 | Kaufhold et al. |
| 2003/0073895 A1 | 4/2003 | Nields et al. |
| 2003/0095624 A1 | 5/2003 | Eberhard et al. |
| 2003/0097055 A1 | 5/2003 | Yanof et al. |
| 2003/0149364 A1* | 8/2003 | Kapur .................. A61B 8/483 600/439 |
| 2003/0169847 A1 | 9/2003 | Karellas et al. |
| 2003/0194050 A1 | 10/2003 | Eberhard |
| 2003/0194051 A1 | 10/2003 | Wang et al. |
| 2003/0194121 A1 | 10/2003 | Eberhard et al. |
| 2003/0210254 A1 | 11/2003 | Doan et al. |
| 2003/0212327 A1 | 11/2003 | Wang et al. |
| 2003/0215120 A1 | 11/2003 | Uppaluri et al. |
| 2004/0008809 A1 | 1/2004 | Webber |
| 2004/0066882 A1 | 4/2004 | Eberhard et al. |
| 2004/0066884 A1 | 4/2004 | Hermann Claus et al. |
| 2004/0066904 A1 | 4/2004 | Eberhard et al. |
| 2004/0070582 A1 | 4/2004 | Smith et al. |
| 2004/0094167 A1 | 5/2004 | Brady et al. |
| 2004/0101095 A1 | 5/2004 | Jing et al. |
| 2004/0109529 A1 | 6/2004 | Eberhard et al. |
| 2004/0146221 A1 | 7/2004 | Siegel et al. |
| 2004/0171986 A1 | 9/2004 | Tremaglio, Jr. et al. |
| 2004/0190682 A1 | 9/2004 | Deuringer |
| 2004/0213378 A1 | 10/2004 | Zhou et al. |
| 2004/0247081 A1 | 12/2004 | Halsmer |
| 2004/0264627 A1 | 12/2004 | Besson |

(56) References Cited

U.S. PATENT DOCUMENTS

| | | |
|---|---|---|
| 2004/0267157 A1 | 12/2004 | Miller et al. |
| 2005/0025278 A1 | 2/2005 | Hagiwara |
| 2005/0049521 A1 | 3/2005 | Miller et al. |
| 2005/0063509 A1 | 3/2005 | DeFreitas et al. |
| 2005/0078797 A1 | 4/2005 | Danielsson et al. |
| 2005/0089205 A1* | 4/2005 | Kapur .................. A61B 8/5238 382/128 |
| 2005/0105679 A1 | 5/2005 | Wu et al. |
| 2005/0113681 A1 | 5/2005 | DeFreitas et al. |
| 2005/0113715 A1 | 5/2005 | Schwindt et al. |
| 2005/0117694 A1 | 6/2005 | Francke |
| 2005/0129172 A1 | 6/2005 | Mertelmeier |
| 2005/0133706 A1 | 6/2005 | Eberhard |
| 2005/0135555 A1 | 6/2005 | Claus et al. |
| 2005/0135664 A1 | 6/2005 | Kaufhold et al. |
| 2005/0226375 A1 | 10/2005 | Eberhard et al. |
| 2005/0248347 A1 | 11/2005 | Damadian |
| 2006/0009693 A1 | 1/2006 | Hanover et al. |
| 2006/0030784 A1 | 2/2006 | Miller et al. |
| 2006/0034426 A1 | 2/2006 | Freudenberger |
| 2006/0074288 A1 | 4/2006 | Kelly |
| 2006/0098855 A1 | 5/2006 | Gkanatsios et al. |
| 2006/0109951 A1 | 5/2006 | Popescu |
| 2006/0126780 A1 | 6/2006 | Rotondo |
| 2006/0129062 A1 | 6/2006 | Nicoson et al. |
| 2006/0155209 A1 | 7/2006 | Miller et al. |
| 2006/0210016 A1 | 9/2006 | Francke |
| 2006/0262898 A1 | 11/2006 | Partain |
| 2006/0269041 A1 | 11/2006 | Mertelmeier |
| 2006/0291618 A1 | 12/2006 | Eberhard et al. |
| 2007/0030949 A1 | 2/2007 | Jing et al. |
| 2007/0036265 A1 | 2/2007 | Jing et al. |
| 2007/0076844 A1 | 4/2007 | Defreitas et al. |
| 2007/0078335 A1 | 4/2007 | Horn |
| 2007/0140419 A1 | 6/2007 | Souchay |
| 2007/0223651 A1 | 9/2007 | Wagenaar et al. |
| 2007/0225600 A1 | 9/2007 | Weibrecht et al. |
| 2007/0242800 A1 | 10/2007 | Jing et al. |
| 2008/0019581 A1 | 1/2008 | Gkanatsios et al. |
| 2008/0045833 A1 | 2/2008 | Defreitas et al. |
| 2008/0056436 A1 | 3/2008 | Pack |
| 2008/0101537 A1 | 5/2008 | Sendai |
| 2008/0112534 A1 | 5/2008 | Defreitas et al. |
| 2008/0118023 A1 | 5/2008 | Besson |
| 2008/0130979 A1 | 6/2008 | Ren et al. |
| 2008/0212861 A1 | 9/2008 | Durgan et al. |
| 2008/0285712 A1 | 11/2008 | Kopans |
| 2008/0317196 A1 | 12/2008 | Lmai |
| 2009/0003519 A1 | 1/2009 | Defreitas et al. |
| 2009/0010384 A1 | 1/2009 | Jing et al. |
| 2009/0080594 A1 | 3/2009 | Brooks et al. |
| 2009/0080602 A1 | 3/2009 | Brooks et al. |
| 2009/0135997 A1 | 5/2009 | Defreitas et al. |
| 2009/0141859 A1 | 6/2009 | Gkanatsios et al. |
| 2009/0213987 A1 | 8/2009 | Stein et al. |
| 2009/0237924 A1 | 9/2009 | Ladewig |
| 2009/0238424 A1 | 9/2009 | Arakita et al. |
| 2009/0268865 A1 | 10/2009 | Ren et al. |
| 2009/0296882 A1 | 12/2009 | Gkanatsios et al. |
| 2009/0304147 A1 | 12/2009 | Jing et al. |
| 2010/0020937 A1 | 1/2010 | Hautmann |
| 2010/0020938 A1 | 1/2010 | Koch |
| 2010/0034450 A1 | 2/2010 | Mertelmeier |
| 2010/0054400 A1 | 3/2010 | Ren |
| 2010/0086188 A1 | 4/2010 | Ruth |
| 2010/0091940 A1 | 4/2010 | Ludwig et al. |
| 2010/0150306 A1 | 6/2010 | Defreitas et al. |
| 2010/0189227 A1 | 7/2010 | Mannar |
| 2010/0195882 A1 | 8/2010 | Ren |
| 2010/0226475 A1 | 9/2010 | Smith |
| 2010/0290585 A1 | 11/2010 | Eliasson |
| 2010/0303202 A1 | 12/2010 | Ren |
| 2010/0313196 A1 | 12/2010 | De Atley et al. |
| 2011/0026667 A1 | 2/2011 | Poorter |
| 2011/0069809 A1 | 3/2011 | Defreitas et al. |
| 2011/0178389 A1 | 7/2011 | Kumar et al. |
| 2011/0188624 A1 | 8/2011 | Ren |
| 2011/0234630 A1 | 9/2011 | Batman et al. |
| 2011/0268246 A1 | 11/2011 | Dafni |
| 2012/0033868 A1 | 2/2012 | Ren |
| 2012/0051502 A1 | 3/2012 | Ohta et al. |
| 2012/0236987 A1 | 9/2012 | Ruimi |
| 2012/0238870 A1 | 9/2012 | Smith et al. |
| 2013/0028374 A1 | 1/2013 | Gkanatsios et al. |
| 2013/0211261 A1 | 8/2013 | Wang |
| 2013/0272494 A1 | 10/2013 | DeFreitas et al. |
| 2014/0044230 A1 | 2/2014 | Stein et al. |
| 2014/0044231 A1 | 2/2014 | Defreitas et al. |
| 2014/0086471 A1 | 3/2014 | Ruth et al. |
| 2014/0098935 A1 | 4/2014 | Defreitas et al. |
| 2014/0232752 A1 | 8/2014 | Ren et al. |
| 2014/0314198 A1 | 10/2014 | Ren et al. |
| 2014/0321607 A1 | 10/2014 | Smith |
| 2014/0376690 A1 | 12/2014 | Jing et al. |
| 2015/0049859 A1 | 2/2015 | DeFreitas et al. |
| 2015/0160848 A1 | 6/2015 | Gkanatsios et al. |
| 2015/0310611 A1 | 10/2015 | Gkanatsios et al. |
| 2016/0106383 A1 | 4/2016 | Ren et al. |
| 2016/0189376 A1 | 6/2016 | Bernard |
| 2016/0209995 A1 | 7/2016 | Jeon |
| 2016/0220207 A1 | 8/2016 | Jouhikainen |
| 2016/0256125 A1 | 9/2016 | Smith |
| 2016/0270742 A9 | 9/2016 | Stein et al. |
| 2016/0302746 A1 | 10/2016 | Erhard |
| 2016/0331339 A1 | 11/2016 | Guo |
| 2017/0024113 A1 | 1/2017 | Gkanatsios et al. |
| 2017/0032546 A1 | 2/2017 | Westerhoff |
| 2017/0071562 A1 | 3/2017 | Suzuki |
| 2017/0128028 A1 | 5/2017 | DeFreitas et al. |
| 2017/0135650 A1 | 5/2017 | Stein et al. |
| 2017/0316588 A1 | 11/2017 | Homann |
| 2017/0319167 A1 | 11/2017 | Goto |
| 2018/0130201 A1 | 5/2018 | Bernard |
| 2018/0177476 A1 | 6/2018 | Jing et al. |
| 2018/0188937 A1 | 7/2018 | Gkanatsios et al. |
| 2018/0289347 A1 | 10/2018 | DeFreitas et al. |
| 2019/0059830 A1 | 2/2019 | Williams |
| 2019/0095087 A1 | 3/2019 | Gkanatsios |
| 2019/0200942 A1 | 7/2019 | DeFreitas |
| 2019/0336794 A1 | 11/2019 | Li |
| 2019/0388051 A1 | 12/2019 | Morita |
| 2020/0029927 A1 | 1/2020 | Wilson |
| 2020/0352531 A1 | 11/2020 | Smith |
| 2021/0128087 A1 | 5/2021 | DeFreitas |

FOREIGN PATENT DOCUMENTS

| | | |
|---|---|---|
| DE | 102004051401 | 5/2006 |
| DE | 102004051820 | 5/2006 |
| DE | 102010027871 | 10/2011 |
| EP | 0775467 | 5/1997 |
| EP | 0982001 | 3/2000 |
| EP | 1028451 | 8/2000 |
| EP | 1428473 | 6/2004 |
| EP | 1759637 | 3/2007 |
| EP | 1569556 | 4/2012 |
| EP | 2732764 | 5/2014 |
| EP | 2602743 | 11/2014 |
| EP | 2819145 | 12/2014 |
| EP | 3143935 | 3/2017 |
| JP | 53151381 U | 11/1978 |
| JP | 2001-346786 | 12/2001 |
| JP | 2002219124 | 8/2002 |
| JP | 2006-231054 | 9/2006 |
| JP | 2007-50264 | 3/2007 |
| JP | 2007-521911 | 8/2007 |
| JP | 2007229269 | 9/2007 |
| JP | 2008-67933 | 3/2008 |
| JP | 200886471 | 4/2008 |
| JP | 2009500048 | 1/2009 |
| JP | 2012-509714 | 4/2012 |
| JP | 2012-511988 | 5/2012 |
| JP | 2015-530706 | 10/2015 |
| WO | WO 90/05485 | 5/1990 |

(56) References Cited

FOREIGN PATENT DOCUMENTS

| WO | WO 9803115 | 1/1998 |
|---|---|---|
| WO | WO 98/16903 | 4/1998 |
| WO | WO 00/51484 | 9/2000 |
| WO | WO 2000068863 | 11/2000 |
| WO | WO 03/020114 | 3/2003 |
| WO | 03037046 | 5/2003 |
| WO | WO 2003/057564 | 7/2003 |
| WO | WO 2004/043535 | 5/2004 |
| WO | WO 2005/051197 | 6/2005 |
| WO | WO 2005/110230 | 11/2005 |
| WO | WO 2005/112767 | 12/2005 |
| WO | WO 2006/055830 | 5/2006 |
| WO | WO 2006/058160 | 6/2006 |
| WO | WO 2007129244 | 11/2007 |
| WO | WO 2008072144 | 6/2008 |
| WO | WO 2009122328 | 10/2009 |
| WO | WO 2009136349 | 11/2009 |
| WO | WO 2010/070554 | 6/2010 |
| WO | WO 2013/184213 | 12/2013 |

OTHER PUBLICATIONS

Thurfjell, E. "Mammography screening: one versus two views and independent double reading." Acta Radiologica 35, No. 4 (1994): 345-350.*

Initial Determination on Violation of Section 337 and Recommended Determination on Remedy and Bond, Public Version, United States International Trade Commission, Washington, D.C, Inv. No. 337-Ta-1063, in the matter of Certain X-Ray Breast Imaging Devices and Components Thereof, dated Jul. 26, 2018, 299 pages.

Decision Denying Institution of Inter Partes Review in case IPR2018-00651 (U.S. Pat. No. 7,831,296 B2), in the matter of *Fujifilm Corporation, Fujfilm Medical Systems USA, and Fujifilm Techno Products Co., Ltd.* (Petitioner) v. *Hologic, Inc.*, (Patent Owner), dated Aug. 21, 2018, 21 pages.

Petition for Inter Partes Review of the U.S. Pat. No. 7,831,296, *Fujifilm Corp. et al.* v. *Hologic Inc.*, 85 pages.

Corrected Petition for Inter Partes Review of the U.S. Pat. No. 7,831,296, *Fujifilm Corp. et al.* v. *Hologic Inc.*, 85 pages.

Ex. 1001 Declaration of Dr. John Allison, 169 pages.

Ex. 1002 Curriculum Vitae of Dr. John Allison, 7 pages.

Ex. 1003 U.S. Pat. No. 7,831,296 ("The '296 Patent"), 13 pages.

Ex. 1004 Patent File History for the '296 Patent, 379 pages.

Ex. 1005 U.S. Pat. No. 7,123,684 ("The '684 Patent"), 11 pages.

Ex. 1006 U.S. Pat. No. 5,872,828 to Loren T. Niklason et al. ("Niklason"), 14 pages.

Ex. 1007 *Development and Clinical Evaluation of Tomosynthesis for Digital Mammography* by Daniel B. Kopans, M.D. ("Kopans"), 91 pages.

Ex. 1008 *Tomosynthesis Breast Imaging: Early Detection and Characterization of Breast Cancer* by Leena M. Hamberg, PhD ("Hamberg"), 20 pages.

Ex. 1009 U.S. Patent Application Publication No. 2002/0090055 naming Albert Zur, et al. as inventors ("Zur"), 11 pages.

Ex. 1010 U.S. Pat. No. 4,613,982 to Dornheim, et al. ("Dornheim"), 4 pages.

Ex. 1011 U.S. Pat. No. 6,632,020 to Kaufhold, et al. ("Kaufhold"), 15 pages.

Ex. 1012 E-mail dated Nov. 1, 2017 from Carol E. Jacobsen, Chief, Customer Support Division, Directorate of User Services, Defense Technical Information Center, 2 pages.

Ex. 1013 Archived copies of public webpages, dated Aug. 2000, on the Defense Technical Information Center's website obtained from the Internet Archive, 8 pages.

Ex. 1014 Archived copies of public webpages, dated Aug. 2000, on the website of National Technical Information Services ("NTIS") obtained from the Internet Archive, 15 pages.

Ex. 1015 Affidavit of Christopher Butler, Office Manager of the Internet Archive, dated Dec. 28, 2017, 2 pages.

Ex. 1016 Print out of web page showing search results for Kopans in the NTIS collection, 2 pages.

Ex. 1017 U.S. Pat. No. 8,452,379 (the "'379 Patent"), 12 pages.

Ex. 1018 Bushberg JT, Seibert JA, Leidholdt EM and Boone JM, The Essential Physics of Medical Imaging, 2nd edition. Philadelphia, PA: Lippincott Williams & Wilkins 2002 (excerpts), 23 pages.

Ex. 1019 "Automatic breast region extraction from digital mammograms for PACS and telemammography applications" by S.L. Lou et al. published in Computerized Medical Imaging and Graphics 2000; 24:205-220 ("Lou"), 16 pages.

Ex. 1020 Instrumentarium Imaging, "Diamond Breast Care," copyright 2003, 20 pages.

Ex. 1021 "Digital Tomosynthesis in Breast Imaging," Loren T. Niklason, PhD, et al., Radiology 1997; 205:399-406 ("Niklason"), 8 pages.

Ex. 1022 Dobbins, J.T., Godfrey, D.J., "Digital x-ray tomosynthesis: Current state of the art and clinical potential," Phys. Med. Biol. 2003 vol. 48:R65-R106, 42 pages.

Ex. 1023 Japanese Patent Application Publication No. H08-186762 identifying Shinichi Yamada and Seiichiro Nagai as inventors ("Yamada"), 41 pages.

Ex. 1024 Certified translation of Yamada, 42 pages.

Ex. 1025 U.S. Pat. No. 6,751,285 to Jeffrey Wayne Eberhard ("Eberhard"), 11 pages.

Ex. 1026 U.S. Pat. No. 6,611,575 to Abdalmajeid Musa Alyassin, et al. ("Alyassin"), 12 pages.

Ex. 1027 S. Vedantham et al., "Digital Breast Tomosynthesis: State of the Art," Radiology 277(3), 663-684, 22 pages.

Ex. 1028 Ingrid Reiser & Stephen Glick, Tomosynthesis Imaging (2014) (excerpts), 8 pages.

Ex. 1029 U.S. Pat. No. 4,542,521 to Hahn, et al. ("Hahn"), 4 pages.

Ex. 1030 U.S. Pat. No. 6,434,218 to Matsumoto ("Matsumoto"), 26 pages.

Ex. 1031 Japanese Utility Model Patent Publication No. S58-16640, identifying Shigekazu Hara et al. as inventors ("Hara"), 10 pages.

Ex. 1032 Certified translation of Hara, 11 pages.

Ex. 1033 Declaration of Frances Cheever, dated Feb. 14, 2018, 3 pages.

Decision Instituting Inter Partes Review in case IPR2018-00672 (Patent 8,452,379 B2), in the matter of *Fujifilm Corporation, Fujfilm Medical Systems USA, and Fujifilm Techno Products Co., Ltd.* (Petitioner) v. *Hologic, Inc.*, (Patent Owner), dated Sep. 4, 2018, 17 pages.

Decision Denying inter Partes Review in case IPR2018-00538 (U.S. Pat. No. 7,123,684 B2), in the matter of *Fujifilm Corporation,* (Petitioner) v. *Hologic, Inc.*, (Patent Owner), dated Jul. 27, 2018, 31 pages.

Kachelriess, Marc et al., "Flying Focal Spot (FFS) in Cone-Beam CT", 2004 IEEE Nuclear Science Symposium Conference Record, Oct. 16-22, 2004, Rome Italy, vol. 6, pp. 3759-3763.

Petition for Inter Partes Review of the U.S. Pat. No. 8,452,379, *Fujifilm Corp. et al.* v. *Hologic Inc.*, 88 pages.

Ex. 1001 Declaration of Dr. John Allison, 168 pages.

Ex. 1003 U.S. Pat. No. 8,452,379 (the '379 Patent), 13 pages.

Ex. 1004 Patent File History for the '379 Patent, 265 pages.

Ex. 1006 U.S. Pat. No. 5,872,828 to Loren T. Niklason et al. ("Niklason") Ex. 1007 *Development and Clinical Evaluation of Tomosynthesis for Digital Mammography* by Daniel B. Kopans, M.D. ("Kopans"), 14 pages.

Ex. 1011 Patent File History for U.S. Pat. No. 7,831,296, 379 pages.

Ex. 1014 Archived copies of public webpages, dated Aug. 2000, on the website of National Technical Information Services ("NTIS") obtained from the Internet Archive, 14 pages.

Ex. 1016 Print out of web page showing search results for Kopans and Hamberg in the NTIS collection, 2 pages.

Ex. 1017 Bushberg JT, Seibert JA, Leidholdt EM and Boone JM, The Essential Physics of Medical Imaging, 2nd edition. Philadelphia, PA: Lippincott Williams & Wilkins 2002 (excerpts), 23 pages.

Ex. 1018 "Automatic breast region extraction from digital mammograms for PACS and telemammography applications" by S.L. Lou et al. published in Computerized Medical Imaging and Graphics 2000; 24:205-220 ("Lou"), 16 pages.

(56) References Cited

OTHER PUBLICATIONS

Ex. 1019 Instrumentarium Imaging, "Diamond Breast Care," copyright 2003, 20 pages.
Ex. 1020 "Digital Tomosynthesis in Breast Imaging," Loren T. Niklason, PhD, et al., Radiology 1997; 205:399-406 ("Niklason"), 8 pages.
Ex. 1021 Dobbins, J.T., Godfrey, D.J., "Digital x-ray tomosynthesis: Current state of the art and clinical potential," Phys. Med. Biol. 2003 vol. 48:R65-R106, 42 pages.
Ex. 1022 Japanese Patent Application Publication No. H08-186762 identifying Shinichi Yamada and Seiichiro Nagai as inventors ("Yamada"), 41 pages.
Ex. 1023 Certified translation of Yamada, 42 pages.
Ex. 1024 U.S. Pat. No. 6,751,285 to Jeffrey Wayne Eberhard ("Eberhard"), 11 pages.
Ex. 1025 U.S. Pat. No. 6,611,575 to Abdalmajeid Musa Alyassin, et al. ("Alyassin"), 12 pages.
Ex. 1026 S. Vedantham et al., "Digital Breast Tomosynthesis: State of the Art," Radiology 277(3), 663-684, 22 pages.
Ex. 1027 Ingrid Reiser & Stephen Glick, Tomosynthesis Imaging (2014) (excerpts), 8 pages.
Ex. 1028 U.S. Pat. No. 4,542,521 to Hahn, et al. ("Hahn"), 4 pages.
Ex. 1029 U.S. Pat. No. 6,434,218 to Matsumoto ("Matsumoto"), 26 pages.
Ex. 1030 Japanese Utility Model Patent Publication No. S58-16640, identifying Shigekazu Hara et al. as inventors ("Hara"), 10 pages.
Ex. 1031 Certified translation of Hara, 11 pages.
Ex. 1032 Declaration of Frances Cheever, dated Feb. 14, 2018, 3 pages.
"Essentials for life: Senographe Essential Full-Field Digital Mammography system", GE Health-care Brochure, MM-0132-05.06-EN-US, 2006, 12 pgs.
"Filtered Back Projection," (Nygren) published May 8, 2007; URL:http://web.archive.org/web/19991010131715/http://www.owlnet.rice.edu/-.about.e1e0539/Projects97/cult/node2.html., 2 pgs.
"Lorad Selenia" Document B-BI-SEO US/Intl (May 2006) copyright Hologic 2006, 12 pgs.
Acrin website, located at https://www.acrin.org/PATIENTS/ABOUTIMAGINGEXAMSANDAGENTS/ABOUTMAMMOGRAPHYANDTOMOSYNTHESIS.aspx, "About Mammography and Tomosnythesis", obtained online on Dec. 8, 2015, 5 pgs.
American College of Radiology website, located at http://www.acr.org/FAQs/DBT-FAQ, "Digital Breast Tomosynthesis FAQ for Insurers", obtained online on Dec. 8, 2015, 2 pages.
Arfelli, F. et al., "Mammography with synchrotron radiation: phase-detection techniques", Apr. 2000, retrieved at: https://www.ncbi.nlm.nih.gov/pubmed/10751500, 8 pages.
Aslund, Magnus, "Digital Mammography with a Photon Counting Detector in a Scanned Multislit Geometry", Doctoral Thesis, Dept of Physics, Royal Institute of Technology, Stockholm, Sweden, Apr. 2007, 51 pages.
Boone, J. et al., "Dedicated Breast CT: Radiation Dose and Image Quality Evaluation", Dec. 31, 2001, retrieved at: http://pubs.rsna.org/doi/abs/10.1148/radiol.2213010334,11 pages.
Chan, Heang-Ping et al., "ROC study of the effect of stereoscopic imaging on assessment of breast lesions", Medical Physics, vol. 32, No. 4, Apr. 2005, 7 pgs.
Cole, Elodia, et al., "The Effects of Gray Scale Image Processing on Digital Mammography Interpretation Performance", Academic Radiology, vol. 12, No. 5, pp. 585-595, May 2005.
Digital Clinical Reports, Tomosynthesis, GE Brochure 98-5493, Nov. 1998, 8 pgs.
Dobbins, James T., "Digital x-ray tomosynthesis: current state of the art and clinical potential," Physics in Medicine and Biology, Taylor and Francis LTD, London GB, vol. 48, No. 19, Oct. 7, 2003, 42 pages.
Federica Pediconi et al., "Color-coded automated signal intensity-curve for detection and characterization of breast lesions: Preliminary evaluation of a new software for MR-based breast imaging", International Congress Series 1281 (2005) 1081-1086.

Grant, David G., "Tomosynthesis: a three-dimensional imaging technique", IEEE Trans. Biomed. Engineering, vol. BME-19, #1, Jan. 1972, pp. 20-28.
Hamberg, Leena M., "Tomosynthesis breast imaging: early detection and characterization of breast cancer", prepared by Massachusetts General Hospital for the U.S. Army Medical Research and Material Command Fort Detrick, Maryland, Jul. 2000, 20 pages.
Japanese Office Action mailed in Application 2016-087710, dated Mar. 1, 2017, 5 pages.
Japanese Office Action mailed in Application 2017-001579, dated Mar. 29, 2017, 1 page. (No English Translation.).
Kapur, Ajay et al., "Combination of Digital Mammography with Semiautomated 3D Breast Ultrasound", Aug. 1, 2004, retrieved at: http://journals.sagepub.com/doi/abs/10.1177/153303460400300402, 10 pages.
Kita et al., "Correspondence between different view breast X-rays using simulation of breast deformation", Proceedings 1998 IEE Computer Society Conference on Computer Vision and Pattern Recognition, Santa Barbara, CA, Jun. 23-25, 1998, pp. 700-707.
Kopans, D., "Development and Clinical Evaluation of Tomosynthesis for Digital Mammography", Oct. 31, 2000, retrieved at: http://oai.dtic.mil/oai/oai?verb=getRecord&metadataPrefix=html&identifier=ADA387722, 91 pages.
Kopans, Daniel B., "Breast Imaging", Chapter 26: Future Advances in Breast Imaging, 2nd Edition, Lippincott-Raven Publishers, Philadelphia, 1998, 37 pages.
Lehmann, V. et al., "MEMS techniques applied to the fabrication of anti-scatter grids for X-ray imaging", 2002, retrieved at: https://www.researchgate.net/profile/S_Ronnebeck/publication/222546207_MEMS_techniques_applied_to_the_fabrication_of anti-scatter_grids_for_Xray_imaging/links/5570136f08aeccd777417301/MEMS-techniques-applied-to-the-fabrication-of-anti-scatter-grids-for-X-ray-imaging.pdf, 6 pages.
Mammographic Accreditation Phantom, http://www.cirsinc.com/pdfs/015cp.pdf. (2006), 2 pgs.
Niklason et al., "Digital Breast Imaging: Tomosynthesis and Digital Subtraction Mammography", Breast Disease, vol. 10, No. 3-4, pp. 151-164, 1998.
Niklason, Loren T. et al., "Digital Tomosynthesis in Breast Imaging", Radiology, Nov. 1997, vol. 205, No. 2, pp. 399-406.
Nykanen, Kirsi et al., "X-ray scattering in full-field digital mammography", Jul. 2003, retrieved at: http://www.siltanen-research.net/publ/NykanenSiltanen2003.pdf, 10 pages.
Pisano, Etta D., "Digital Mammography", Radiology, vol. 234, No. 2, Feb. 2005, pp. 353-362.
Senographe 700 & 800T (GE); 2-page download on Jun. 22, 2006 from www.gehealthcare.com/inen/rad/whe/products/mswh800t.html.; Figures 1-7 on 4 sheets re lateral shift compression paddle, 2 pgs.
Smith, A., "Fundamentals of Breast Tomosynthesis", White Paper, Hologic Inc., WP-00007, Jun. 2008, 8 pgs.
Smith, Andrew, PhD, "Full Field Breast Tomosynthesis", Hologic White Paper, Oct. 2004, 6 pgs.
Suryanarayanan, S. et al., "Comparison of tomosynthesis methods used with digital mammography", Dec. 31, 2000, retrieved at: http://www.sciencedirect.com/science/article/pii/S1076633200800616, 13 pages.
Suryanarayanan, S. et al., "Evaluation of Linear and Nonlinear Tomosynthetic Reconstruction Methods in Digital Mammography", Mar. 2001, retrieved at: http://www.sciencedirect.com/science/article/pii/S1076633203805305, 6 pages.
Webber, Richard, "A controlled evaluation of tuned-aperture computed tomography applied to digital spot mammography", Feb. 2000, retrieved at: https://www.ncbi.nlm.nih.gov/pmc/articles/PMC3453191/, 8 pages.
Wheeler F. W., et al. "Micro-Calcification Detection in Digital Tomosynthesis Mammography", Proceedings of SPIE, Conf— Physics of Semiconductor Devices, Dec. 11, 2001 to Dec. 15, 2001, Delhi, SPIE, US, vol. 6144, Feb. 13, 2006, 12 pgs.
Wu, T. et al., "A comparison of reconstruction algorithms for breast tomosynthesis", Aug. 26, 2004, retrieved at: http://onlinelibrary.wiley.com/doi/10.1118/1.1786692/full.

(56) References Cited

OTHER PUBLICATIONS

Wu, Tao, et al. "Tomographic Mammography Using a Limited Number of Low-Dose Cone-Beam Projection Images" Medical Physics, AIP, Melville, NY, vol. 30, No. 3, Mar. 1, 2003, p. 365-380.
Japanese Notice of Rejection in Application 2018-554775, dated Feb. 22, 2021, 10 pages.

* cited by examiner

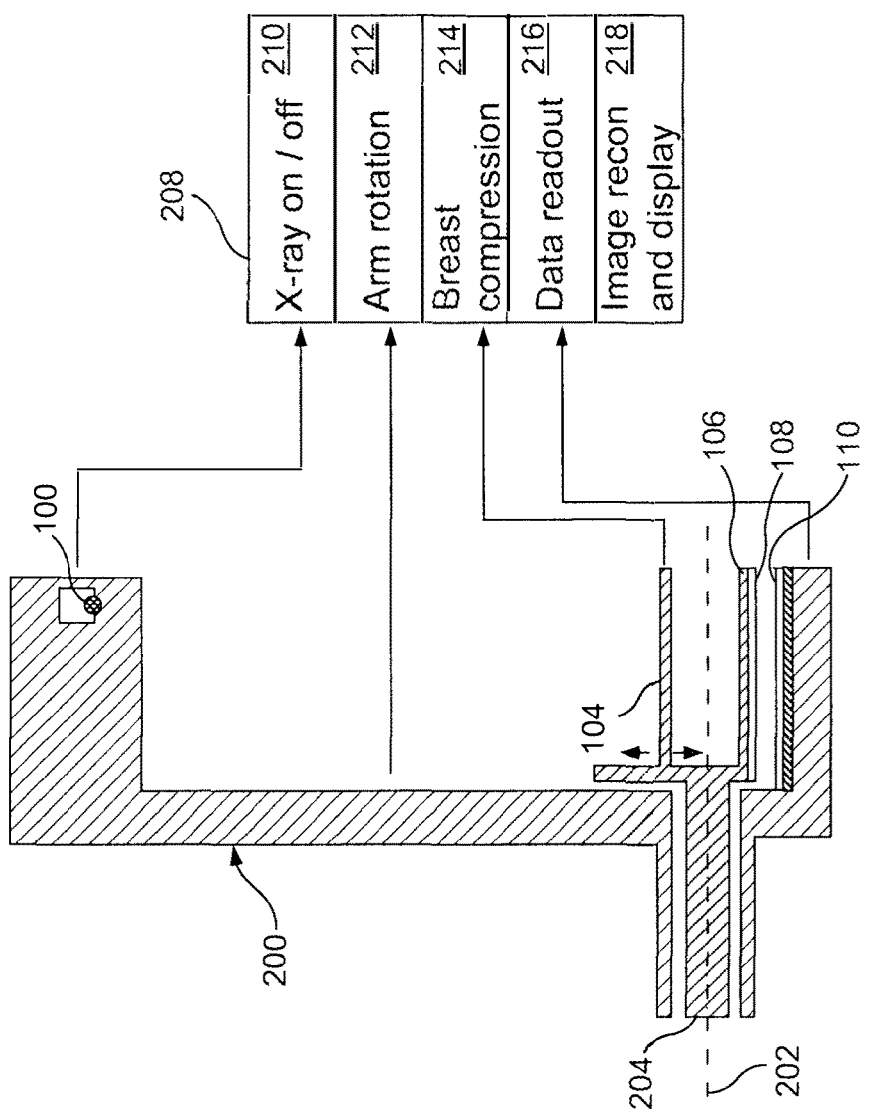
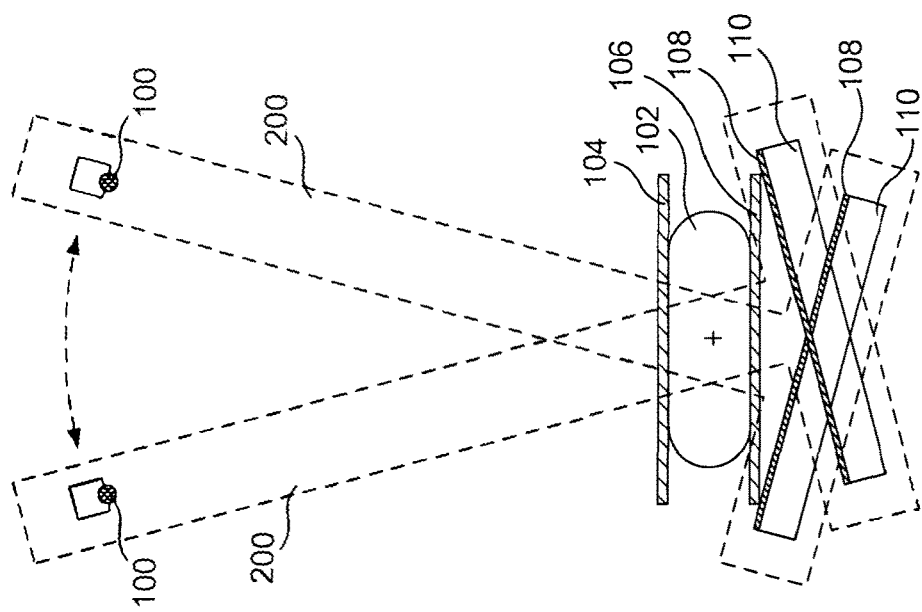
FIG. 8
FIG. 7

X-RAY MAMMOGRAPHY WITH TOMOSYNTHESIS

CROSS REFERENCE TO RELATED APPLICATIONS

This application is a continuation of U.S. patent application Ser. No. 13/896,828, filed May 17, 2013, entitled "X-RAY MAMMOGRAPHY WITH TOMOSYNTHESIS", now U.S. Pat. No. 10,638,994, which is a continuation of U.S. patent application Ser. No. 12/879,807, filed Sep. 10, 2010, now U.S. Pat. No. 8,452,379, which is a divisional of U.S. patent application Ser. No. 10/723,486, filed Nov. 26, 2003, now U.S. Pat. No. 7,831,296; the disclosures of which are hereby incorporated by reference herein in their entireties.

FIELD

This patent specification is in the field of x-ray imaging of the breast and, more specifically, obtaining and processing x-ray data for tomosynthesis.

BACKGROUND

Breast cancer remains an important threat to women's health. X-ray mammography currently is the most widely used breast imaging tool for early detection, and is the modality approved by the Food and Drug Administration to screen for breast cancer in women who do not show symptoms of breast disease. A typical mammography system takes a projection image of the compressed breast, using a collimated x-ray source at one side and a film/screen unit at the other side of the breast. In the United States, typically two views are taken of each breast, one from above (cranial-caudal, or CC) and one from the side (mediolateral-oblique, or MLO). The x-ray source is an x-ray tube typically operating at 25-40 kVp, using a molybdenum or rhodium rotating anode with a focal spot of about 0.3-0.4 mm and, in some cases, 0.1 mm or less. An anti-scatter grid between the breast and the film/screen unit reduces the effects of x-ray scatter. The screen converts x-ray energy to visible light to which the film is exposed to record the image. In each view, the breast is compressed to reduce patient motion and also for reasons such as reducing scatter, separating overlapping structures in the breast, making the thickness of the imaged breast more uniform, and providing more uniform x-ray exposure. Currently, flat panel array receptors are replacing the film/screen units in mammography systems. The Selenia™ digital mammography system with such a flat panel x-ray receptor is offered by Lorad, a subsidiary of the assignee Hologic, Inc. of Bedford, Mass. Digital mammography has significant advantages and in time may fully supplant film/screen systems. Additional information regarding digital mammography systems and processes offered by the common assignee can be found at <www.hologic.com>.

Mammograms, whether from film/screen units or from digital systems, are particularly difficult to read, and the rate of false negatives and false positives is significant. Many advances have been made in recent years in image acquisition and in image processing, but a need still remains to reduce the rates of false negatives and positives, at least in screening mammography. Additional information can be gained through modalities such as CT and MRI, but examination and interpretation time and cost and other factors have limited their use in screening for breast cancer. Ultrasound breast examination has been proposed as an adjunct to x-ray examination, with synthesized ultrasound images of thick slices of the breast as they would appear in the same projection view as an x-ray view displayed together with the x-ray view, and a unit taking both x-ray and ultrasound images has been proposed. See, e.g., Patent Application Publication No. U.S. 2003/0007598 A1 and U.S. Pat. No. 5,983,123. Digital tomosynthesis has been proposed for x-ray breast imaging, and a laboratory unit is believed to have been installed at the Massachusetts General Hospital (more than a year before the filing date hereof), as reported in Wu, Tao, 2002, *Three-Dimensional Mammography Reconstruction Using Low Dose Projection Images*, PhD thesis, Brandeis University, incorporated here by reference. See, also, Patent Application Publication No. 2001/0038681 A1 and PCT application International Publication No. WO 03/020114 A2 published Mar. 13, 2003, both incorporated herein by reference. Digital tomosynthesis in more general contexts also has been proposed. See, e.g., U.S. Pat. Nos. 6,289,235 and 5,051,904, commonly assigned U.S. Pat. No. 4,496,557, and Digital Clinical Reports, Tomosynthesis. GE Brochure 98-5493, 11/98, all incorporated herein by reference. Reference markers can be used in x-ray imaging for purposes such as checking the rotation angle and unwanted shift of center of rotation of an x-ray source and receptor, and fiducial phantoms can be used in 3D angiography to calibrate for irregular scan geometries. See, e.g., U.S. Pat. Nos. 5,051,904, 5,359,637, and 6,289,235, N. Navab, et al., *Dynamic geometrical calibration for 3D cerebral angiography*, SPIE Vol. 2708, pp. 361-370, and said PCT published application WO 03/020114 A2, all incorporated by reference here.

It is believed that no breast tomosynthesis systems are commercially available currently for clinical use in breast imaging, and that improvements in x-ray imaging and tomosynthesis are a desired goal. Accordingly, it is believed that a need remains for improved and practical tomosynthesis mammography.

SUMMARY

In a typical x-ray imaging according to preferred embodiments disclosed in this patent specification, a patient's breast is immobilized, at the same or lower compression than in conventional mammography, between a breast platform and a compression paddle. The platform and paddle, and the breast between them, in turn are between an x-ray source and a digital imaging receptor. Unlike conventional x-ray mammography, in which typically a breast is imaged from only one angle at a given compression, here the immobilized breast is imaged with x-rays from the source that pass through the breast and impinge on the receptor, from a greater number of different positions of the source and receptor relative to the breast while maintaining the breast immobilized, to derive image data for the respective positions. To do this, the x-ray source moves around the immobilized breast, typically but not necessarily in an arc, and the receptor also moves relative to the breast, but in a motion that allows it to remain substantially parallel to the same plane. The x-ray data taken at each of a number of positions of the receptor relative to the breast is processed to form images where each of a number of the images is formed from image data acquired from two or more of the different positions, e.g., to form tomosynthetic images. The x-ray dose to the breast can be different for the different imaging positions. One or more of the imaging positions can use an x-ray dose comparable to that used for conventional mammography. These positions may be the same or similar to the source/receptor positions for the typical views used in conventional mammography, e.g., the CC view and the MLO view. Fiducial markers can be used to help assess the positions of the x-ray source and x-ray receptor relative to each other and/or the breast being imaged, and for other calibration purposes. The fiducial markers can be integrated with the compression paddle and/or the breast platform, or can be positioned otherwise to serve the intended purpose. The immobilized breast can be imaged at angular positions extending over a selected range around the immobilized breast, for example ±15°, although other ranges can be used in other examples. The motion can be continuous over some or all of the imaging positions, or can be intermittent such that the x-ray source and/or the x-ray receptor stop for taking and image and then move to the next position for the next image.

An antiscatter grid can be used, positioned between the breast platform and the x-ray receptor while x-ray image data are taken. One example is the grid available from Lorad under the tradename HTC® grid. Alternatively, the image data at some or all of the imaging positions can be taken without an antiscatter grid that is external to the x-ray receptor. Rather than using the currently conventional materials for the x-ray emitting target in an x-ray tube serving as the x-ray source, in one of the preferred embodiments the target is made essentially of Tungsten, to provide x-rays at energies that are believed more suitable for breast x-ray tomosynthesis. Geometries other than an x-ray source that rotates around the immobilized breast and an x-ray receptor that moves relative to the breast and the source but remains in substantially parallel to the same plane, can be used.

Image data taken at the different imaging positions can be processed to generate tomosynthetic images of selected slices of the breast. The images can be of thin slices, essentially planar sections through the breast, as in CT slices. Alternatively, they can be of thick slices of the breast, e.g., slices that are about 0.5 cm to about 1.0 cm thick, and simulate projection images of slices of that thickness, projected on one or more selected image planes. In one example, the image plane or planes of the thick slice images are the same as those of the typical conventional mammograms, and can be displayed for viewing in appropriate groupings. For example, projection-like tomosynthetic images of thick slices on a plane parallel to that of a conventional CC image can be displayed together with a conventional CC image of a breast, on the same screen or adjacent screens or other displays. Similarly, projection-like tomosynthetic images of thick slices on plane parallel to that of an MLO image can be displayed on the same display or on adjacent displays with a conventional MLO mammogram of the same breast. In the alternative, the image planes of the tomosynthetic images can be at one or more selected angles to the image planes of the typical images used in screening x-ray mammography.

Tomosynthetic images can be formed using a form of filtered backprojection modified by using a filter function that is significantly different from a conventional ramp filter used in CT technology backprojection. The novel filter function is believed to be uniquely suited to breast tomosynthesis. In particular, in the frequency domain the novel filter function at low spatial frequencies is much steeper than a CT technology ramp function, it is close to an all-pass filter at intermediate frequencies, and at higher frequencies it falls off to suppress fine detail noise.

BRIEF DESCRIPTION OF THE DRAWING

FIGS. 7 and 8 are similar to FIGS. 1 and 2, respectively, but illustrate another preferred embodiment.

DETAILED DESCRIPTION OF PREFERRED EMBODIMENTS

Figure 1:
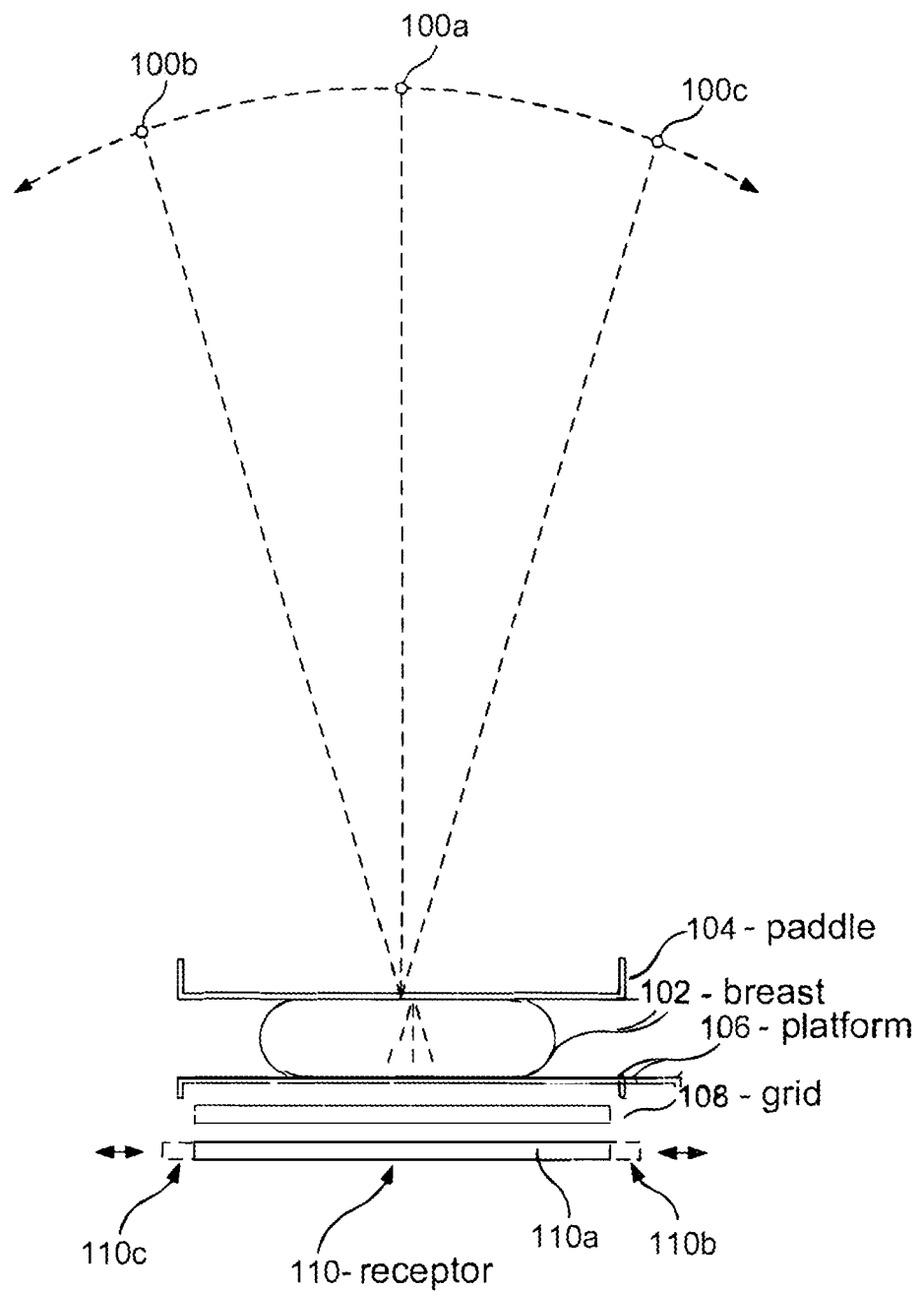
FIG. 1 illustrates schematically a front view of an x-ray source, a breast immobilized between a compression paddle and a breast platform, an antiscatter grid and an image receptor, where the x-ray source and the x-ray receptor move relative to the breast for imaging the breast at different angles according to a preferred embodiment.

FIG. 1 schematically illustrates in front view an x-ray source 100 in three different positions 100a, 100b and 100c, between which source 100 moves in an arc centered at the top center of a patient's breast 102 immobilized between a compression paddle 104 and a breast platform 106. An antiscatter grid 108 is immediately below breast platform 106, and an x-ray receptor 110 is below grid 108, and is shown in three different positions, 110a, 110b, and 110c, corresponding to the illustrated positions of source 100. Receptor 110 moves relative to immobilized breast 102 along a path substantially parallel to breast platform 106 and maintains substantially the same distance from platform 106, as indicated by the arrows in FIG. 1. In operation, source 100 moves from one of its illustrated position to another, and so does receptor 110. At each position of source 100 and receptor 110, source 100 is energized to emit a collimated x-ray beam, of which only the center ray is illustrated. The beam irradiates breast 102 and some of the radiation that has passed through the breast also passes through grid 108 and is received by receptor 110. As in known in the art, receptor 110 and associated electronics generate image data in digital form for each pixel of a rectangular grid of pixels at each of the illustrated angular position of source 100 and translation positions of receptor 110 relative to immobilized breast 102. While only three positions are illustrated in FIG. 1, in practice image data is taken at each of a much greater number of positions, for example, at every 1° of an arc of ±15° of source 100 around immobilized breast 102. The taking of image data can be while source 100 and receptor 110 are stopped at their respective positions, after moving from one position to the next. In a different preferred embodiment, the motion of one or both of source 100 and receptor 110 can be continuous, with a respective set of image data being accumulated over a small increment of continuous motion, say a 0.1° to 0.5° arc of motion of source 100. These parameters are only an example. Different preferred embodiments can use different ranges of motion of source 100 and receptor 110, and can use a motion of source 100 that is arcuate and centered at a different point, such as in immobilized breast 102 or at breast platform 106 or at grid 108 or at receptor 110, or a motion that is not arcuate but is translational or is a combination of different types of motions, such as partly translational and partly rotational. In the most preferred embodiment, the source 100 motion is arcuate and the receptor 110 motion is translational. As described further below, in practice source 100 can be integrated in a C-arm that is the same or similar to the C-arm used in the commercially available Selenia® or MIV mammography systems available from Lorad, and receptor 110 can be the same receptor as used in such commercially available systems but mounted differently so that it translates in a plane substantially parallel to breast platform 106 while maintaining a substantially constant distance from platform 106 rather that rotating as a unit with source 100, as in Lorad commercially available systems.

Figure 2:
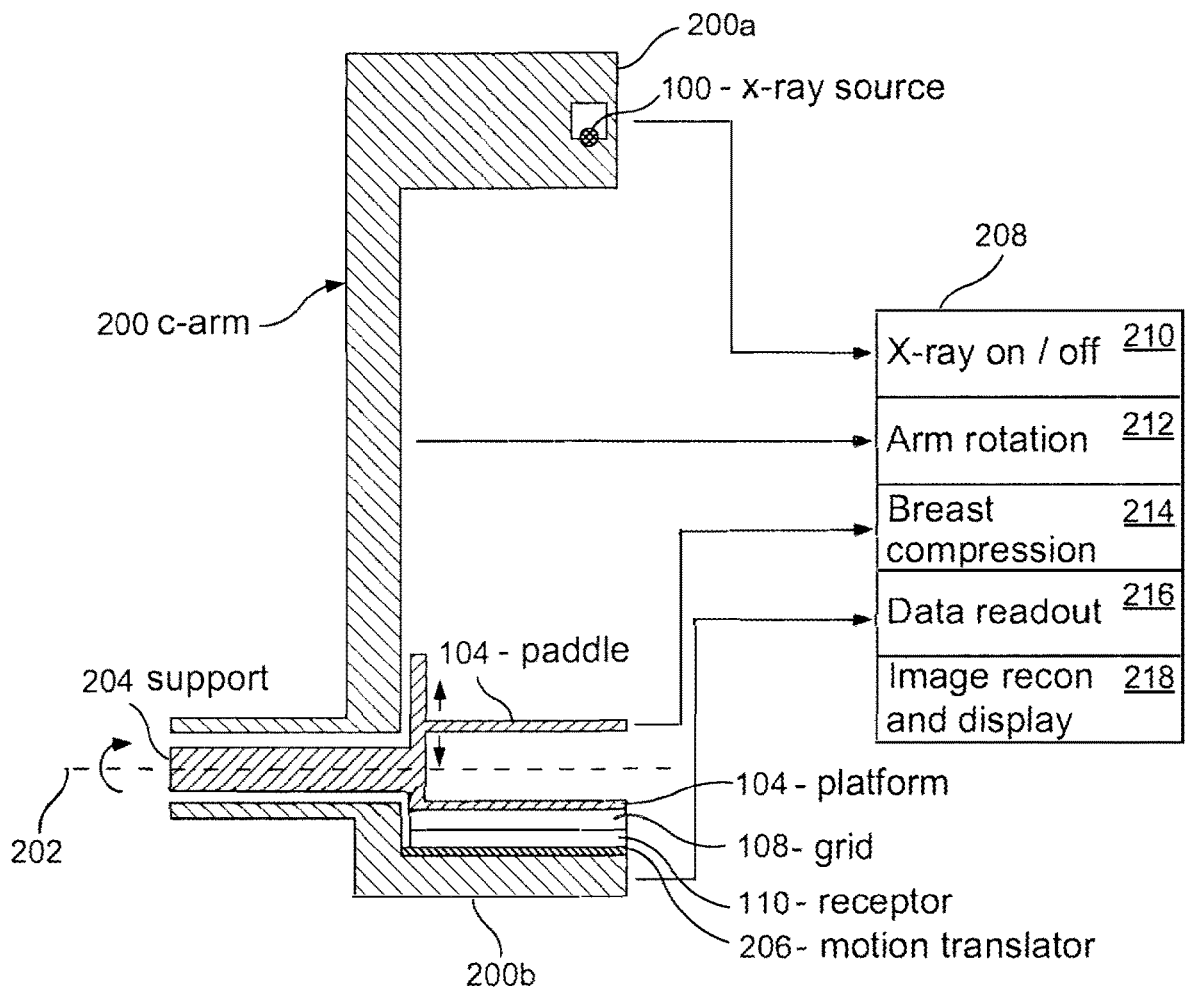
FIG. 2 illustrates a side view of the system illustrated in FIG. 1 and additional components of a system according to a preferred embodiment.

FIG. 2 schematically illustrates a side view of a mammography system using the arrangement of FIG. 1. In FIG. 2, x-ray source 100 is at one end 200a of a C-arm 200 that is supported for selective rotation about an axis 202, independently of a support 204 for compression paddle 104 and breast platform 106. Support 204 also selectively rotates about the same axis 202. The other end 200b of C-arm 200 interacts with x-ray receptor 110 through a motion translator schematically illustrated at 206 that translates the rotational motion of the end 200b about axis 202 to a substantially translational motion of receptor 110 that substantially maintains the distance of receptor 110 from breast platform 106 while x-ray data is being taken. FIG. 2 is not to scale, and receptor 110 can be spaced further from member 200b than illustrated, to allow more space for motion translator 206, and also to allow for receptor 110 to be moved selectively further from or closer to breast platform 104 and thus allow for x-ray image magnification. In operation, C-arm 200 and support 204 are rotated to desired angular positions, either manually or by motor drives, patient breast 102 is positioned on platform 106 and is immobilized by bringing paddle 104 toward platform 106 and compressing breast 102, with typically the same or less force than for a typical conventional mammogram, such as between one to one-third the conventional force. With breast 102 immobilized, and with C-arm at a selected angle relative to a normal to platform 106 and receptor 110, such as +15°, imaging starts, and a projection image is taken for each of a number of selected angular positions of source 100 while C-arm 200 rotates, continuously or intermittently, through a selected angle, such as an angle of 30°, is from +15° to −15°. Of course, the motion can be in the opposite direction, from −15° to +15°, or can be over a different angular interval, such as over less than a total of 30°, e.g. 25°, 20°, etc., or more than 30°, such as 35°, 40°, etc. Currently, the preferred range is 115°. A set of image data can be taken at selected angular positions, such as every degree, or every fraction of a degree, or every several degrees of angle. The angular increments between the different positions for sets of image data need not be the same. For example, the increments around 0° can be less than those at the extremes of the angular positions, or vice versa. Currently, the preferred angular increment is 3°. The sets of image data can be taken after an incremental motion from one angular position of source 100 to another, and from one translational position of receptor 110 to another, such that source 100 and receptor 110 are stationary while a set of image data is being taken. Alternatively, one or both of source 100 and receptor 110 can move continuously while sets of image data are being taken, one set for each increment of continuous motion. In the currently preferred embodiment, in the example of continuous motion while taking image data both source 100 and receptor 110 move while image data are being taken.

FIG. 2 also illustrates schematically an electrical/electronic system 208 that interacts with the components discussed above. System 208 includes a control 210 for selectively energizing and otherwise controlling x-ray source 100, an arm rotation control 212 for selectively rotating C-arm 200 and support 204, a breast compression control 214 for selectively moving compression paddle 104 toward and away from breast platform 106, data readout electronics 216 coupled with x-ray receptor 110 to read out the sets of image data at the respective positions of source 100 and receptor 110 relative to immobilized breast 102, and an image reconstruction and display unit 218 coupled with data readout electronics 216 to receive the sets of image data from electronics 216 and to process the image data for reconstruction and other purposes and display images.

For a given position of breast 102, such as a position that is the same or similar to the CC position for a conventional mammogram, source 100 and receptor 110 can be positioned relative to immobilized breast 102 such that at the 0° position a center ray of the x-ray beam from source 100 would be substantially normal to receptor breast platform 106 and receptor 110. For a first set of image data, source 100 is at +(or −) 15° in a preferred example, and is gradually moved, continuously or intermittently to − (or +) 15°, with a set of image data taken every 3°. The angular range and the increment over which data sets are taken can each be selectively set by the operator, depending of characteristics of the breast being imaged and the screening and diagnostic needs, and can be different for different patients or from one to the other breast of the same patient. For example the source can move through angles that range from a fraction to a degree to several degrees from one imaging position to the next. Each set of image data is supplied by image readout 216 for processing at image reconstruction and display unit 218. Each set of image data can be taken at the same x-ray dose to the breast, and the dose at any one of the different imaging positions can be substantially less than that for a conventional mammogram. The x-ray dose can be substantially the same for each imaging position, but preferably the dose at one of the position, e.g., at or close to the 0° position, is the same or similar to dose for a conventional mammogram while the dose at the each of the other positions is less, preferably much less. Alternatively, the scan can begin with or end with an exposure close to the 0° position at a dose similar to a conventional mammogram, and the rest of the set of image data can be over the angular range with each exposure at an x-ray dose that is substantially less than that for a conventional mammogram. Thus, two types of images can be produced in accordance with the currently preferred embodiment while breast 102 is immobilized in the same position. One type is the same or is at least similar to a conventional mammogram, which can be read and interpreted in the manner familiar to health professionals. The other type is tomosynthetic images reconstructed from the image data and displayed either separately or as an adjunct to the display of the image that is the same or similar to a conventional mammogram. The process described above for one position of breast 102 can be repeated for another position. For example one process can be for a breast position in a manner that is the same or similar to positioning the breast for a conventional CC view, the breast can then be released, the support 204 and C-arm 200 rotated to other angular positions and the breast repositioned in a manner that is the same and similar to the position for an MLO view, and the procedure repeated.

Figure 3:
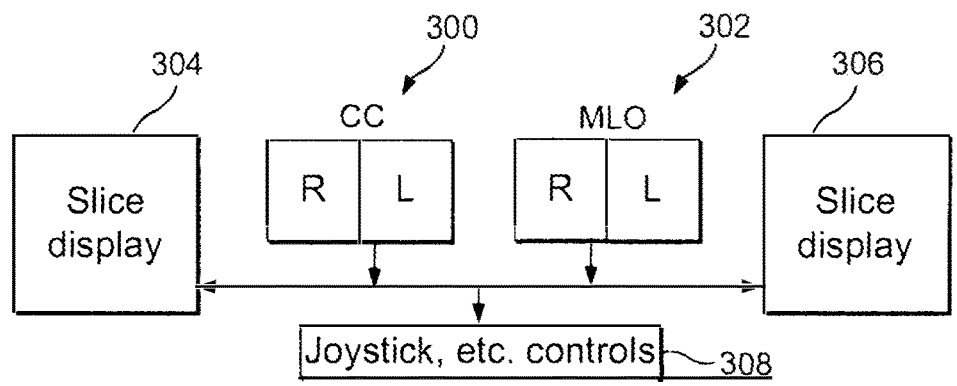
FIG. 3 illustrates a display arrangement showing both images that are the same or similar to conventional mammograms and tomosynthetic images according to a preferred embodiment.

FIG. 3 illustrates schematically a display according to a preferred embodiment, where 300 is a display that is the same or similar to a display for a conventional CC mammogram of two breasts and 302 is a similar display for a conventional MLO view. Another display 304 is close to display 300 and can display any one or more of several types of tomosynthetic images reconstructed from the image data taken at the different imaging positions. For example, if display 300 shows views of a right breast taken at or close to the 0° position in one imaging sequence of a total rotation of source 100 over the ±15° range, display 304 can show, at the option of the user, any one or more of the following views of the right breast: (1) one or more of the projection views taken at the different imaging positions; (2) one or more of several tomosynthetic views of thick slices of the right breast simulating projection views of the right breast taken at the same or similar angle as the view at display 300, with the slices having effective thicknesses selected by the user, such as from several mm to something less than the thickness of the immobilized breast, typically from several mm to about 1 cm; (3) one or more tomosynthetic views of thin slices of the right breast, each simulating a slice through the breast in a respective plane parallel to that of the view at display 300, where each thin slice has an effective thickness of about a mm or less; (4) thin and/or thick slices corresponding to planes that are not parallel to that of the view at display 300; (5) a scrolling image through any of the slices discussed above; and (6) a selected combination of the above displays. A similar display 306 can be associated with display 302, and show a similar selected views related to the images at display 302. FIG. 3 illustrates only one example according to preferred embodiments. Other arrangements also are contemplated, such as different windows on the same display for the different images, differently positioned displays, etc. The user can select the type of images for display, the thickness of a thick slice or a thin slice, the orientation of the slices for display, which slices to display where and in what order, whether to display thick or thin slices as static slides or to scroll through slice images as in movie, etc. Controls 306 can be coupled to each of the displays, and can include manual inputs such as a joystick and/or other known interface devices and a suitably programmed computer to allow a user to control the images that are displayed. For example, the controls can include: (1) selecting one or more areas or volumes of interest at one or more of the displayed images and further processing the image data to form and display additional images of the area or volume of interest (for example, if a lesion is identified that is between tomosynthetic thin slices 32 and 37, the user can manually designate the corresponding area or volume and command the display of the thin slices in that area or volume, and other parameters such as the orientation of the thin slices); (2) identifying the position of an area or region of interest for use in additional procedures such as needle biopsy (for example, the user can designate with a cursor or in some other way a point in or an outline of a suspected lesion in the breast, and the xyz coordinates of the designated point, area, or volume); (3) the user can manually designate the desired thickness, arrangement, and other parameters of slices whose images are to be displayed, to thereby display images of slices that have user-selected thicknesses and other parameters, such as orientation, so that images of slices of different thicknesses and/or orientations can be displayed concurrently; and (4) the user can point to an area of interest in one of the displayed images and the system can automatically display one or more markers at corresponding or at least related locations in one or more of the other images that are being concurrently displayed.

At each imaging position, receptor 100 generates respective digital values for the pixels in a two-dimensional array. In one example, receptor 110 has a rectangular array of approximately 4096 by 3328 pixels, with a pixel size of approximately 70 micrometers in each of the column and row directions. The image data of a set (for a respective imaging position) can be processed either at the full spatial resolution of receptor 110, or at a lower effective spatial resolution, e.g., by binning several original pixel value's into a single, combined pixel value. For example, each set of 2×2 adjacent pixels can be combined into a single respective pixel value, thus achieving an effective spatial resolution of 140 micrometers in each direction. The binning can be in some other combination of original pixels, such as 2×3, and can be done by data readout electronics 216 or image reconstruction and display unit 218 (FIG. 2).

Figure 4:
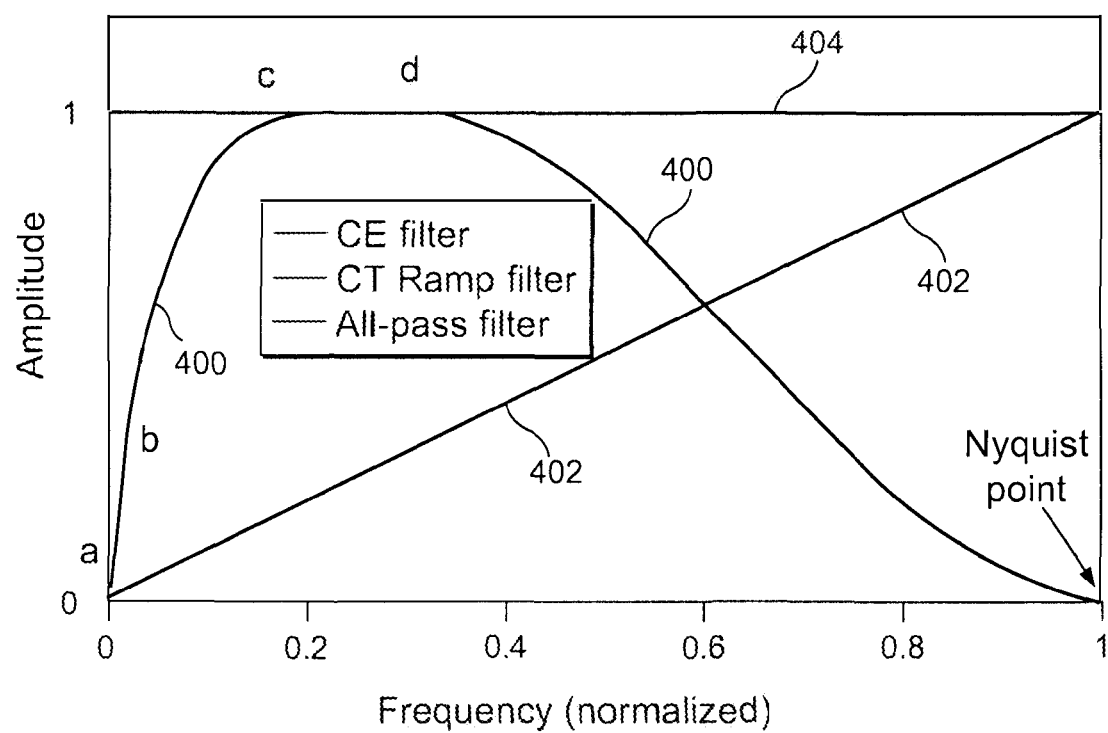
FIG. 4 illustrates in graph form a backprojection filter in the frequency domain used in a preferred embodiment, compared with a conventional ramp filter used in CT technology and an all-pass filter.

Image reconstruction is done using backprojection in the spatial domain or in the frequency domain as in CT technology but with a novel filter that differs from the ramp filter (in the frequency domain) used in CT reconstruction. See, e.g., G. Lauritsch, et al., *A theoretical framework for filtered backprojection in tomosynthesis*, SPIE Medical Imaging Conference, Vol. 3338, 1998, and U.S. Pat. No. 6,442,288, both incorporated here by reference. Referring to FIG. 4, the novel filter is represented by graph 400, while a graph 402 represents a conventional CT ramp filter, and a graph 404 represents an all-pass filter. As seen in FIG. 4, the novel filter according to a preferred embodiment rises sharply in amplitude at lower frequencies, between points a and c (in the range indicated at b), as compared with the conventional ramp filter, then levels off at intermediate frequencies to become the same as or close to an all-pass filter between points c and d, and then gradually drops off at higher frequencies. Using the novel filter produces significantly better breast images compared to using a conventional CT technology ramp filter.

Figure 5:
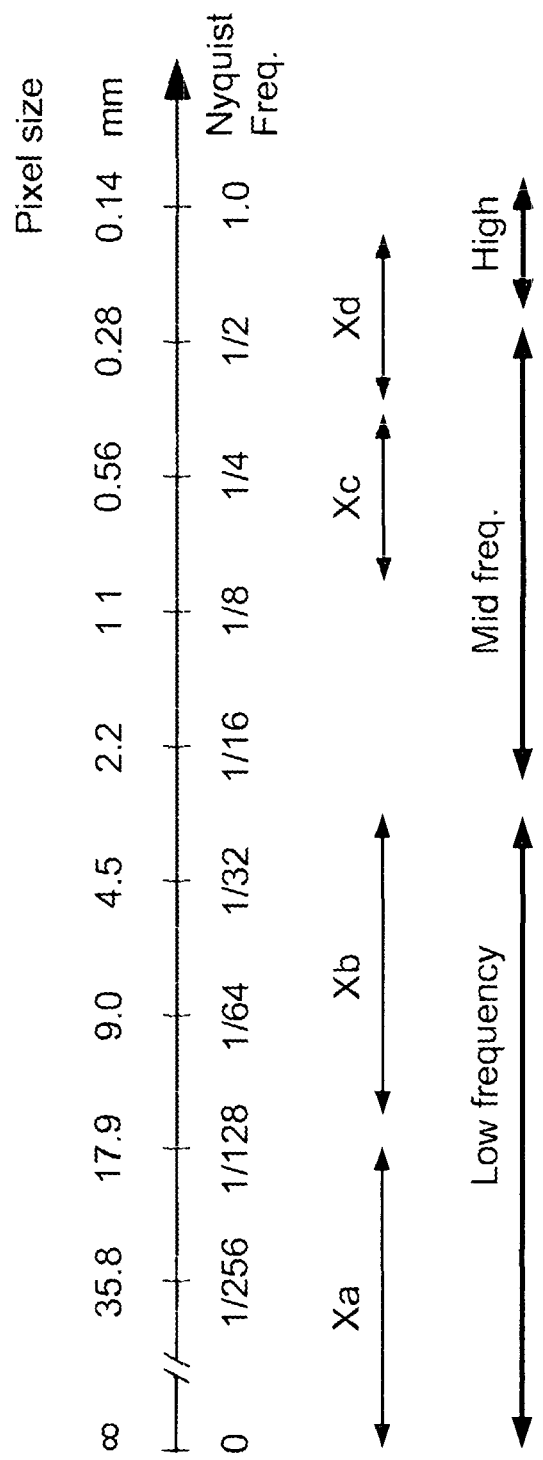
FIG. 5 illustrates coordinate values of a backprojection filter according to a preferred embodiment as control point values in the frequency domain in log scale.

FIG. 5 gives a sense of the values of the low, intermediate and high frequencies discussed in connection with FIG. 5. In FIG. 5, the frequency axis is plotted on log scale, and typically is related to spatial resolution of a few mm or more, i.e., it affects mainly to overall impression and flatness of the reconstructed image. With suitable suppression of low frequency content through frequency dependent weights defined by the shape of the novel filter, and gradual suppression of high frequency noise, a tomographic image with good image contrast at all frequency scales can be reconstructed and presented in accordance with a preferred embodiment. Preferably, the filtered backprojection reconstruction of tomographic images is carried out in the frequency domain, using well known processes with the novel filter. However, comparable filtered backprojection can be carried out in the spatial domain, as in known in CT technology, using direct convolution of image data with the spatial domain representation of the filter represented in the frequency domain in FIGS. 4 and 5. In either the frequency domain or in the spatial domain the novel filter can be applier to the image data to generate filtered data for backprojection, or backprojection can be carried out first, followed by a filtering operation. The reconstruction process preferably uses the direct fan-beam backprojection method known in CT technology, but with the novel filter, although it may be possible to use the image data to simulate sets of parallel beam paths for backprojection. The reconstructed thin slice images form a three-dimensional image of the breast, comprising voxel values for respective incremental volumes. These voxel values can then be combined as known in CT technology to synthesize any selected thin slice or thick slice in any selected orientation, and in any selected projection plane.

In a preferred embodiment, while each of all or most of the imaging positions uses lower x-ray dose than that of a conventional mammogram, higher KV can be used as compared with a conventional mammogram in order to boost signal levels from receptor 110 and improve signal-to-noise (SNR) ratios. In addition, preferable an x-ray tube with a Tungsten target is used to further exploit the advantage of higher kVp imaging of the breast, such as between 25 and 50 kVp with different x-ray beam filtration. A small focal spot, of the order of 1 mm or less, is preferred, although a larger focal spot of several mm can be used.

In other preferred embodiments, contrast enhanced breast tomosynthesis can be carried out, by obtaining tomosynthetic images as described above before injecting a contrast agent such as Iodine into the patient, then repeating the process after injection, and subtracting images of the pre-injection and post-injection sets. Another preferred embodiment involves time subtraction tomosynthesis, related to subtracting comparable images obtained at different times. Yet another is dual-energy breast tomosynthesis, whereby two tomosynthetic images at low and high energies are acquired and then subtracted, the two images being acquired through a process such as using successive scans at two different x-ray energy ranges or by alternating x-ray pulses of low and high energy to create the two images. Another other preferred embodiment involves obtaining and displaying both x-ray tomosynthetic images of a breast and ultrasound images of the same breast. Computer aided diagnosis, as known to those skilled in the art and as commercially used currently in the United States, can be applied to selected tomosynthetic images generated as described above.

Figure 6:
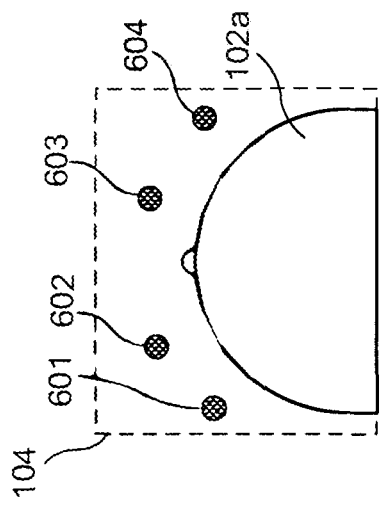
FIG. 6 illustrates the use of fiducial markers.

Fiducial markers are used in preferred embodiments for off-line (without a breast) mechanical positioning and calibration and/or on-line (while imaging a breast with x-rays) image based positioning encoding of moving components. The fiducial markers can be made of a material such as lead or another metal, and can be in the form of points or lines or arrows or crosses, at locations that would be imaged by the x-ray beam at receptor 110 simultaneously with the imaging of a breast 102 but outside the area of the breast image. The fiducial markers are integrated with compression paddle 104, or they can be at or near breast platform 106, or they can be supported separately from paddle 104, for example on a separate member that can be selectively brought into the path of the imaging x-ray beam or taken out of that path, e.g., to take an image that is the same or similar to a conventional mammogram. Different patterns or types of fiducial markers can be provided, for selection by the user. FIG. 6 illustrates an example of arranging fiducial markers 601, 602, 603 and 604 relative to an image of breast 102a on receptor 110, as seen in a top plan view when receptor 110 is horizontal and the fiducial markers are integrated in compression paddle 104.

An alternative embodiment, illustrated schematically in a front view in FIG. 7 and in side view in FIG. 8, is similar to the embodiment illustrated in FIGS. 1 and 2 except that receptor 110 is affixed to the end 200b of C-arm 200 that is opposite x-ray source 100. In this embodiment, receptor 110 moves relative to immobilized breast 102 along an arcuate path from one imaging position to another. Because the change in angle between receptor 110 and breast platform is small, it can be disregarded in processing the sets of x-ray image data. Alternatively, a geometric correction known to those skilled in the art can be applied to each set of image data to convert it to interpolated pixel values that would correspond to those that would have been obtained if receptor 110 had been parallel to and at the same distance from platform 106 at all imaging positions. The so corrected sets of image data can then be used in filtered back projections as described above.

In each of the embodiments of FIGS. 1-2 and FIGS. 7-8, antiscatter grid 108 may be selectively retractable, so that the user may take any selected set of x-ray image data with or without using grid 108. As in known in the art, grid 108 can be made to move relative to the x-ray beam during the taking of a set of image data. Similarly, the distance between breast platform 106 and receptor 110 can be selectively changed to effect magnification of the breast image recorded at receptor 110.

The invention claimed is:

1. A method comprising:
providing an x-ray source configured to move relative to a patient's breast, a flat panel digital x-ray imager, and a breast support and a compression paddle positioned between the x-ray source and the x-ray imager, wherein the compression paddle is configured for compressing the breast against the breast support;
compressing the patient's breast between the compression paddle and the breast support;
selectively energizing the x-ray source to emit a plurality of first x-rays through the breast to the imager at a plurality of first x-ray doses;
controlling the imager to derive from the plurality of first x-rays a set of x-ray images of the breast;
receiving a signal identifying an area of interest in the set of x-ray images;
identifying a position within the compressed breast of the area of interest;
selectively energizing the x-ray source to emit a second x-ray through the breast to the imager at a second x-ray dose, wherein the second x-ray dose is different than each of the plurality of first x-ray doses, and wherein selectively energizing the x-ray source comprises emitting a first number of the plurality of first x-rays, emitting the second x-ray, and emitting a second number of the plurality of first x-rays; and
performing a needle biopsy on the area of interest.

2. The method of claim 1, wherein the set of x-ray images comprise a plurality of tomosynthesis x-ray images.

3. The method of claim 2, further comprising controlling the imager to derive from the second x-ray a two-dimensional image of the breast.

4. The method of claim 3, wherein the two-dimensional image of the breast is derived from the second x-ray emitted when the x-ray source is at an angle of about +15° to the breast support.

5. The method of claim 3, wherein the two-dimensional image of the breast is derived from the second x-ray emitted when the x-ray source is at an angle of about 0° to the breast support.

6. The method of claim 3, wherein the two-dimensional image of the breast comprises a plurality of two-dimensional images of the breast.

7. The method of claim 1, wherein selectively energizing the x-ray source to emit the second x-ray is performed prior to performing the needle biopsy.

8. The method of claim 1, wherein selectively energizing the x-ray source to emit the second x-ray is performed prior to selectively energizing the x-ray source to emit the plurality of first x-rays.

9. The method of claim 1, wherein receiving the signal identifying the area of interest in the set of x-ray images comprises receiving a user selection associated with at least one x-ray image of the set of x-ray images.

10. The method of claim 1, wherein each of the plurality of first x-ray doses are less than the second x-ray dose.

11. A method comprising:
providing an x-ray source, a flat panel digital x-ray imager, a breast support and a compression paddle positioned between the source and the imager, and a motor drive for rotating the x-ray source while performing a tomosynthesis imaging procedure, wherein the compression paddle is configured for compressing a patient's breast against the breast support;
compressing the patient's breast between the compression paddle and the breast support;
selectively energizing the x-ray source to emit at least one of (1) a plurality of first x-rays through the breast to the imager at a plurality of first x-ray doses, wherein emitting the plurality of first x-rays comprises performing the tomosynthesis imaging procedure, and (2) a second x-ray through the breast to the imager at a second x-ray dose, wherein each of the plurality of first x-ray doses is different than the second x-ray dose, and wherein selectively energizing the x-ray source comprises emitting a first number of the first x-rays, followed by emitting the second x-ray, followed by emitting a second number of the first x-rays;
controlling the imager to derive from at least one of the plurality of first x-rays and the second x-ray at least one x-ray image;
receiving a signal identifying an area of interest in the compressed breast;
identifying a position within the compressed breast of the area of interest; and
performing a needle biopsy on the area of interest.

12. The method of claim 11, wherein selectively energizing the x-ray source comprises emitting the plurality of first x-rays through the breast to the imager at the plurality of first x-ray doses.

13. The method of claim 11, wherein receiving the signal identifying the area of interest in the compressed breast comprises receiving a user input associated with the at least one x-ray image.

14. The method of claim 11, further comprising providing an anti-scatter grid and positioning the anti-scatter grid based at least in part on the emission of at least one of the (1) plurality of first x-rays and (2) the second x-ray.

15. The method of claim 14, wherein positioning the anti-scatter grid comprises positioning the anti-scatter grid between the x-ray source and the x-ray imager when emitting the plurality of first x-rays.

16. The method of claim 11, wherein identifying the position within the compressed breast of the area of interest is performed before selectively energizing the x-ray source to emit the first x-ray.

17. The method of claim 11, wherein each of the plurality of first x-ray doses are each less than the second x-ray dose.

18. The method of claim 11, wherein selectively energizing the x-ray source to emit the second x-ray occurs prior to performing the needle biopsy.

* * * * *